United States Patent
Ota et al.

(10) Patent No.: US 9,820,648 B2
(45) Date of Patent: Nov. 21, 2017

(54) IMAGE PROCESSING APPARATUS AND IMAGE PROCESSING METHOD

(71) Applicant: CANON KABUSHIKI KAISHA, Tokyo (JP)

(72) Inventors: Yuji Ota, Yokohama (JP); Tomoyuki Iwanaga, Yokohama (JP); Manabu Wada, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 64 days.

(21) Appl. No.: 14/317,393

(22) Filed: Jun. 27, 2014

(65) Prior Publication Data
US 2015/0002813 A1    Jan. 1, 2015

(30) Foreign Application Priority Data

Jun. 28, 2013  (WO) .................. PCT/JP2013/067842

(51) Int. Cl.
| | |
|---|---|
| *A61B 3/14* | (2006.01) |
| *A61B 3/12* | (2006.01) |
| *A61B 3/00* | (2006.01) |
| *A61B 5/00* | (2006.01) |

(52) U.S. Cl.
CPC .............. *A61B 3/12* (2013.01); *A61B 3/0025* (2013.01); *A61B 5/0059* (2013.01)

(58) Field of Classification Search
CPC .... A61B 1/12; A61B 1/13; A61B 1/14; A61B 3/04; A61B 3/117
USPC .................. 351/205, 206, 210, 214, 215
See application file for complete search history.

(56) References Cited

U.S. PATENT DOCUMENTS

| | | | |
|---|---|---|---|
| 7,784,942 B2 * | 8/2010 | Maeda ................ | A61B 3/1241 351/205 |
| 7,856,135 B1 * | 12/2010 | Bernardes ............... | A61B 3/12 382/131 |
| 8,041,091 B2 * | 10/2011 | de Oliveira e Ramos ............... | A61B 3/0041 345/418 |
| 9,089,280 B2 * | 7/2015 | Iwase ..................... | A61B 3/102 |

(Continued)

FOREIGN PATENT DOCUMENTS

| | | |
|---|---|---|
| JP | 4-336677 A | 11/1992 |
| JP | 8-110939 A | 4/1996 |

(Continued)

*Primary Examiner* — Stephone B Allen
*Assistant Examiner* — Travis Fissel
(74) *Attorney, Agent, or Firm* — Canon U.S.A., Inc. IP Division

(57) ABSTRACT

An image processing apparatus includes a generation unit and a display control unit. The generation unit generates a subtraction image using a first region and a second region, the first region being a portion of a first fundus image acquired by performing autofluorescence imaging on a fundus of an eye to be inspected, the second region being a portion of a second fundus image acquired by performing autofluorescence imaging on the fundus of the eye to be inspected at a time different from that of the first fundus image and being at a position corresponding to the first region. The display control unit causes a display unit to display an image generated by superimposing information regarding the subtraction image at a position corresponding to the first and second regions on a fundus image acquired by performing autofluorescence imaging on the fundus.

15 Claims, 7 Drawing Sheets

(56) References Cited

U.S. PATENT DOCUMENTS

| | | | | |
|---|---|---|---|---|
| 2007/0092124 A1* | 4/2007 | Moriya | ............... | G06T 5/50 |
| | | | | 382/128 |
| 2011/0103655 A1* | 5/2011 | Young | ............... | G06T 7/0028 |
| | | | | 382/128 |
| 2011/0164219 A1* | 7/2011 | Ono | ............... | A61B 3/12 |
| | | | | 351/206 |
| 2012/0218516 A1* | 8/2012 | Imamura | ............... | A61B 3/1241 |
| | | | | 351/206 |
| 2012/0239015 A1* | 9/2012 | Liesfeld | ............... | A61B 3/12 |
| | | | | 606/4 |

FOREIGN PATENT DOCUMENTS

| | | | | |
|---|---|---|---|---|
| JP | 2004-329742 A | | 11/2004 | |
| JP | 2005-342282 A | | 12/2005 | |
| JP | 2005342282 A | * | 12/2005 | |
| JP | 2006-247076 A | | 9/2006 | |
| JP | 2007-066130 A | | 3/2007 | |
| JP | 2007-105352 A | | 4/2007 | |
| JP | 2010-279536 A | | 12/2010 | |
| JP | 2005342282 A | * | 12/2015 | ............... A61B 3/14 |

* cited by examiner

I # IMAGE PROCESSING APPARATUS AND IMAGE PROCESSING METHOD

TECHNICAL FIELD

The present invention relates to an image processing apparatus and an image processing method for processing images.

BACKGROUND ART

Recently, fundus autofluorescence imaging (FAF: Fundus Auto-Fluorescence) has been receiving attention. PTL1 has disclosed that, in autofluorescence imaging, the fundus is illuminated with light around 550 nm as excitation light and light around 640 nm is received as autofluorescence caused by lipofuscin. A user may detect age-related macular degeneration or the like at an early stage by checking lipofuscin using a fundus image acquired as a result of this light reception.

In addition, PTL2 has disclosed that a subtraction image is generated by achieving matching for a plurality of fundus images using an optic disk portion and a blood vessel portion in the plurality of fundus images.

CITATION LIST

Patent Literature

PTL 1 Japanese Patent Laid-Open No. 2006-247076
PTL 2 Japanese Patent Laid-Open No. 4-336677

Here, when lipofuscin accumulates near a macula, there is a high probability that age-related macular degeneration will occur. Thus, it is important to check changes in lipofuscin that occur over time. Here, the case is considered where a user checks changes in lipofuscin that have occurred over time using a subtraction image generated using a plurality of fundus images which have been acquired by performing autofluorescence imaging on the fundus. Here, the subtraction image itself does not display a region other than a region where a change in lipofuscin has occurred over time. Thus, it is difficult for a user to determine which portion of a fundus image corresponds to the position of the region where a change in lipofuscin has occurred over time.

An object of the present invention is to facilitate, in the case where a user checks changes in lipofuscin that have occurred over time using a subtraction image, checking of the position of a region where a change in lipofuscin has occurred over time in a fundus image.

SUMMARY OF INVENTION

An image processing apparatus according to the present invention includes generation means that generates a subtraction image using a first region and a second region, the first region being a portion of a first fundus image acquired by performing autofluorescence imaging on a fundus of an eye to be inspected, the second region being a portion of a second fundus image acquired by performing autofluorescence imaging on the fundus of the eye to be inspected at a time different from that of the first fundus image and being at a position corresponding to the first region, and display control means that causes display means to display an image generated by superimposing information regarding the subtraction image at a position corresponding to the first and second regions on a fundus image acquired by performing autofluorescence imaging on the fundus.

Further features of the present invention will become apparent from the following description of exemplary embodiments with reference to the attached drawings.

DESCRIPTION OF EMBODIMENTS

Figure 1:
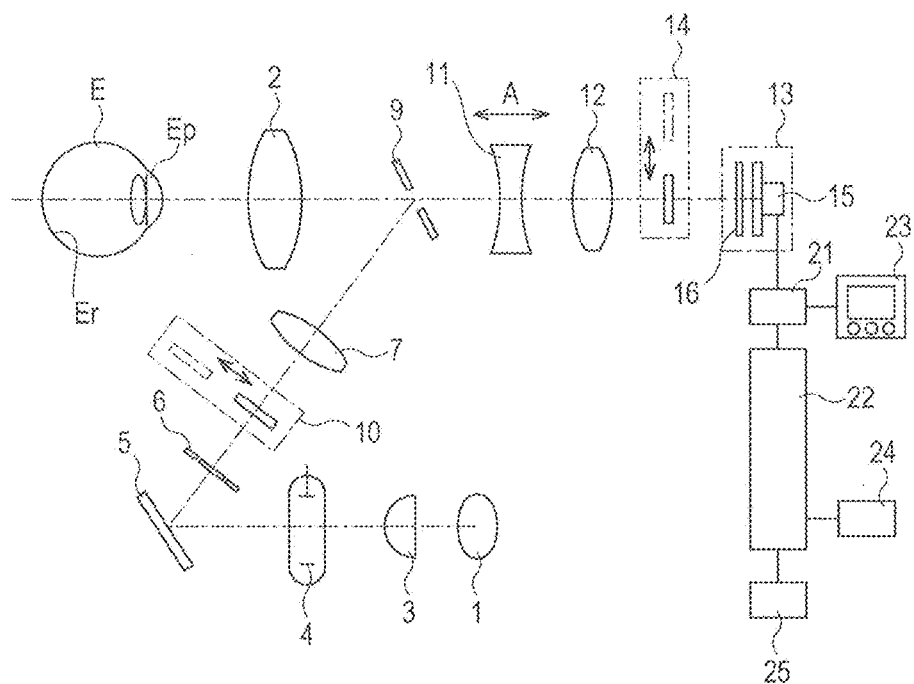
FIG. 1 is a schematic diagram illustrating an example of an entire configuration of a present embodiment.

An image processing apparatus according to a present embodiment includes, first, generation means that generates a subtraction image using a partial region of a first fundus image and a partial region of a second fundus image, the partial regions corresponding to each other, the first fundus image and the second fundus image having been acquired at different times by performing autofluorescence imaging on the fundus of an eye to be inspected. In addition, the generation means generates a subtraction image using a first region and a second region, the first region being a portion of the first fundus image (an example of a first image), the second region being a portion of the second fundus image (an example of a second image) and being at a position corresponding to the first region. Note that the subtraction image is an example of an image illustrating changes in the first and second regions and is also called a third image in a present specification. In addition, the image processing apparatus according to the present embodiment includes display control means that causes display means to display an image generated by superimposing information regarding the subtraction image at a position corresponding to the first and second regions on a fundus image acquired by performing autofluorescence imaging on the fundus. Note that the information regarding the subtraction image may also be, for example, the subtraction image itself, a display form illustrating the position of the subtraction image (for example, a frame of a dotted line or the like), or both. Note that, preferably, the first and second regions are regions where a change in lipofuscin has occurred over time.

As a result, it is easier for a user to determine which portion of a fundus image corresponds to the position of a region where a change in lipofuscin has occurred over time. Thus, in the case where a user checks changes in lipofuscin that have occurred over time using a subtraction image, checking of the position of a region may be facilitated where a change in lipofuscin has occurred over time in a fundus image.

Here, the display control means may cause display means to display a superimposition image, on which a subtraction image has been superimposed at the position in the fundus images. In addition, the display control means may cause the display means to arrange and display a superimposition image, on which a display form illustrating the position has been superimposed at the position in the fundus images, and the subtraction image. Note that, in the present specification, the above-described generation means is also called first generation means and image superimposition means is also called second generation means.

In addition, the generation means generates a subtraction image using first and second fundus images and may also generate, as a subtraction image, a region having an intensity greater than or equal to a certain intensity in the subtraction image generated using the first and second fundus images. In addition, the generation means determines the first and second regions and may also generate, as a subtraction image, a difference image generated using the first and second regions.

In addition, it is preferable that the image processing apparatus according to the present embodiment further include changing means that changes the gradation of at least one of the first and second fundus images on the basis of pixel values of a region which is less likely to be affected by changes in lipofuscin that occur over time in the first and second fundus images, for example, a region including a blood vessel of the fundus. Then, a region where a change in lipofuscin has occurred over time may be clearly displayed by generating a subtraction image after the pixel values of the first region have been made to be almost equal to those of the second region. Note that it is preferable that the above-described changing means change the gradation of the first fundus image such that pixel values of the first region become equal to pixel values of the second region. In addition, it is preferable that the above-described changing means change the gradations of the first and second fundus images such that pixel values of the first and second regions become equal to certain pixel values.

In the following, embodiments of the present invention will be described with reference to drawings.

Description of Apparatus

FIG. 1 is a diagram of the configuration of an ophthalmic imaging apparatus in the present embodiment. As the ophthalmic imaging apparatus in the present embodiment, a fundus camera that captures images of the fundus using a two-dimensional sensor or the like, an OCT apparatus or an SLO apparatus that includes scanning means that scans the fundus with light, or the like is preferably used. Note that, the ophthalmic imaging apparatus in the present embodiment may be any imaging apparatus that captures images of an eye to be inspected. Alternatively, in the case of capturing images of an object to be inspected other than an eye to be inspected, the ophthalmic imaging apparatus in the present embodiment may be any imaging apparatus for medical use such as an endoscope.

First, in the ophthalmic imaging apparatus in the present embodiment, a condenser lens 3, an imaging-use light source 4, a mirror 5, an aperture 6 having a ring-shaped opening, a relay lens 7, and a mirror 9, which has a hole, are sequentially arranged along an optical path from an observation-use light source 1 to an object lens 2 positioned in front of an eye E to be inspected. Furthermore, an autofluorescence exciter filter 10, which is an example of wavelength selection means, is arranged between the aperture 6 and the relay lens 7 such that the autofluorescence exciter filter 10 is insertable into and removable from an optical path between the aperture 6 and the relay lens 7. In this manner, an illumination optical system is configured. Note that the autofluorescence exciter filter 10 allows light of a wavelength range from, for example, about 475 nm to about 615 nm, more preferably, a wavelength range from about 530 nm to about 580 nm to pass therethrough. In addition, preferably, the autofluorescence exciter filter 10 blocks light of wavelengths outside this wavelength range. Here, the autofluorescence exciter filter 10 is inserted into the optical path of the illumination optical system when autofluorescence observation imaging is to be performed (in the case where an autofluorescence imaging mode has been selected from among a plurality of imaging modes by use of selection means, which is not illustrated). In addition, the autofluorescence exciter filter 10 is removed from the optical path of the illumination optical system when color imaging is to be performed. Note that, in the case where an SLO apparatus is used, the illumination optical system may be configured such that light of a wavelength for autofluorescence is used by changing a laser light source, the SLO apparatus having a galvanometer mirror or a resonance scanner, the galvanometer mirror and the resonance scanner being examples of scanning means that performs scanning with measurement light with which the eye E to be inspected is to be illuminated.

In addition, a focus lens 11, an imaging lens 12, and a color imaging unit 13 are arranged along an optical path of the mirror 9, which has a hole, in a light-passing-through direction. In addition, an autofluorescence barrier filter 14 (an example of the wavelength selection means) that blocks autofluorescence excitation light and allows fluorescence to selectively pass therethrough is arranged between the imaging lens 12 and the color imaging unit 13 such that the autofluorescence barrier filter 14 is insertable into and removable from an optical path between the imaging lens 12 and the color imaging unit 13. As a result, an observation imaging optical system is configured. The color imaging unit 13 has an imaging device 15 and a tri-color separation color filter 16. Note that, preferably, the autofluorescence barrier filter 14 allows light of, for example, a wavelength range around 640 nm to pass therethrough and blocks light of wavelengths outside this wavelength range. In particular, preferably, the autofluorescence barrier filter 14 blocks light of wavelengths of excitation light with which lipofuscin is excited (for example, a wavelength range having a range from about 530 nm to about 580 nm). Here, the autofluorescence barrier filter 14 is inserted into the optical path of the observation imaging optical system when autofluorescence imaging is to be performed (in the case where the autofluorescence imaging mode has been selected from among the plurality of imaging modes by use of the selection means, which is not illustrated). In addition, the autofluorescence barrier filter 14 is removed from the optical path of the observation imaging optical system when color imaging is to be performed.

In addition, an output of the imaging device 15 is connected to a system controller 22 via an image signal processing unit 21. In addition, a display 23 is connected to the image signal processing unit 21, an observation image of the eye E to be inspected is displayed, and the eye E to be inspected is observed. Moreover, an image recording unit 24 and an operation switch unit 25 are connected to the system controller 22. As a result, a control system of the entire fundus camera is configured.

When color-image imaging is performed, luminous flux emitted from the observation-use light source 1 passes through the condenser lens 3 and the imaging-use light source 4, and is reflected by the mirror 5. Light reflected from the mirror 5 passes through the aperture 6 and the relay lens 7, is reflected by a portion of the mirror 9 that is not a hole, the mirror 9 having a hole, and passes through the object lens 2, and the fundus Er of the eye E to be inspected is illuminated with visible light. Here, the autofluorescence exciter filter 10 has been removed from the illumination optical system.

Light reflected from the fundus Er passes through the object lens 2 and a hole of the mirror 9, which has a hole, passes through the focus lens 11 and the imaging lens 12, and forms an image on the imaging device 15. Here, since the autofluorescence barrier filter 14 has been removed from the observation imaging optical system for the fundus, the light reflected from the fundus Er may be observed as is, as a fundus image, on the display 23.

While watching this fundus image, an examiner performs alignment for the eye E to be inspected by moving the apparatus frontward/backward, leftward/rightward, and upward/downward using alignment indicators and an operation unit, which are not illustrated. Furthermore, the examiner performs focusing by moving the focus lens 11 using indicators for focusing.

Figure 2A:
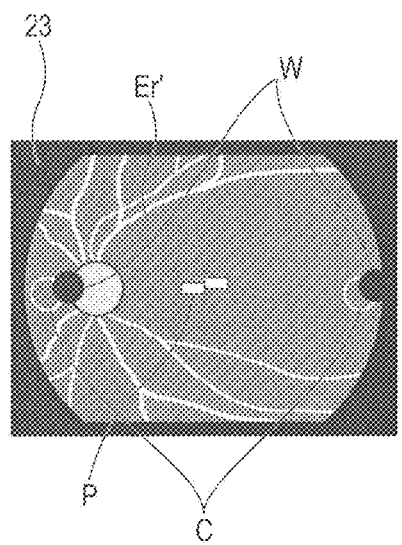
FIGS. 2A and 2B are diagrams associated with alignment and focusing of the present embodiment.
Figure 2B:
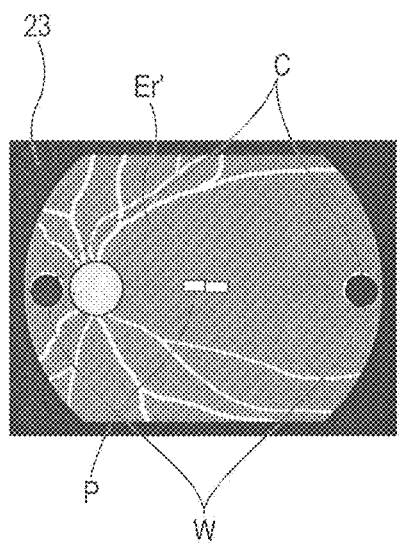

FIGS. 2A and 2B illustrate an observation state of a fundus image Er' on the display 23. FIG. 2A illustrates a state in which alignment and focusing have not been completed yet and in which alignment circles C do not match alignment indicators W and indicators P for focusing do not match either. FIG. 2B illustrates a state in which alignment and focusing have been completed and in which the alignment circles C match the alignment indicators W and the indicators P for focusing are arranged in a straight line.

When the examiner presses an imaging switch of the operation switch unit 25 after completion of alignment for and focusing of the fundus image Er', the system controller 22 causes the imaging-use light source 4 to emit light. Luminous flux emitted from the imaging-use light source 4 and traveling in a path similar to that for luminous flux of the observation-use light source 1 illuminates the fundus Er, and light reflected from the illuminated fundus Er forms an image on the imaging device 15 similarly as in the case of observation. Image data of the formed fundus image Er' is saved as a color image in the image recording unit 24 via the image signal processing unit 21 and the system controller 22, and the fundus image Er' is displayed on the display 23.

When autofluorescence observation is to be performed, the autofluorescence exciter filter 10 is inserted into the illumination optical path. Luminous flux emitted from the observation-use light source 1 passes through the condenser lens 3 and the imaging-use light source 4, and is reflected by the mirror 5. Light reflected from the mirror 5 passes through the aperture 6 and the autofluorescence exciter filter 10, is reflected by a portion of the mirror 9 that is not a hole, the mirror 9 having a hole, and passes through the object lens 2, and the fundus Er is illuminated with visible light.

Light reflected from the illuminated fundus Er passes through a pupil Ep, the object lens 2, and the hole of the mirror 9, which has a hole, passes through the focus lens 11 and the imaging lens 12, and forms an image on the imaging device 15. Here, since the autofluorescence barrier filter 14 has been removed from the observation imaging optical system for the fundus, light reflected from the fundus Er out of light of wavelengths that has passed through the autofluorescence exciter filter 10 may be observed as the fundus image Er'.

While watching this fundus image Er', similarly to as in the case described using FIGS. 2A and 2B, the examiner performs alignment of the apparatus for the eye E to be inspected using the alignment indicators W and performs focusing the indicators P for focusing.

When the examiner presses the imaging switch of the operation switch unit 25 after completion of alignment for and focusing of the fundus image Er', the system controller 22 inserts the autofluorescence barrier filter 14 into the observation imaging optical system for the fundus and causes the imaging-use light source 4 to emit light. Luminous flux emitted from the imaging-use light source 4 travels in a path similar to that for luminous flux of the observation-use light source 1, and then the fundus Er is illuminated with light of a wavelength that has passed through the autofluorescence exciter filter 10. Light reflected from the illuminated fundus Er passes through the pupil Ep, the object lens 2, and the hole of the mirror 9, which has a hole, passes through the focus lens 11 and the imaging lens 12, and the autofluorescence barrier filter 14 blocks light of wavelengths that has passed through the autofluorescence exciter filter 10. As a result, only fluorescence of the fundus image Er' passes and forms an image on the imaging device 15.

The fundus image Er', which has been formed, is changed into a monochrome image by the image signal processing unit 21 and saved as a monochrome image in the image recording unit 24 via the system controller 22. The fundus image Er', which is a monochrome image, is displayed on the display 23. Note that the image signal processing unit 21 may have a function through which a signal from the imaging device 15 is not processed and a signal to and from the system controller 22 and a signal to and from the display 23 are only transferred. In this case, the image signal processing unit 21 and the system controller 22 may also be integrally configured as, for example, an image processing apparatus.

Next, subtraction generation, which is a characteristic of the present embodiment, will be described using FIGS. 3 to 11B. Here, in the present embodiment, an image gradation changing starting unit 601, a region extraction unit 602, an image gradation changing unit 603, and an image gradation changing ending unit 604 are functional blocks inside the system controller 22, which is an example of the image processing apparatus. In addition, in the present embodiment, a subtraction generation starting unit 605, an alignment unit 606, a subtraction generation unit 607, and a subtraction generation ending unit 608 are also functional blocks inside the system controller 22, which is an example of the image processing apparatus. Note that at least one of these functional blocks may be a functional block in the outside such as in the image signal processing unit 21. In addition, these functional blocks are realized using a CPU that the system controller 22 has and a memory in which a program for executing a flowchart to be described below is stored.

Selection of Images

Figure 3:
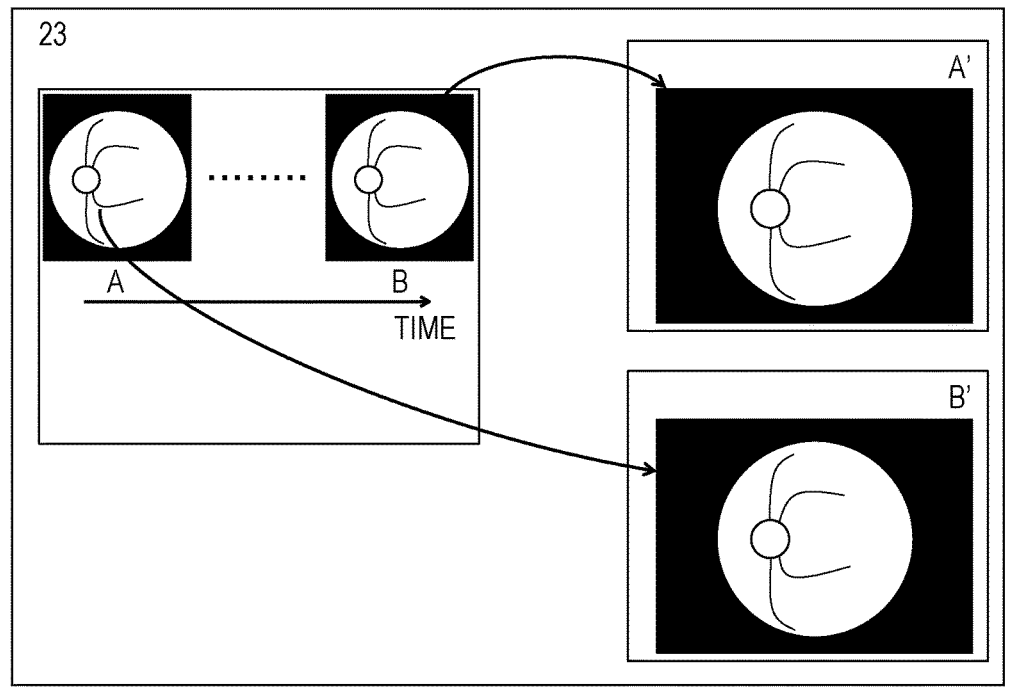
FIG. 3 is a diagram associated with a time when images are selected in the present embodiment.
Figure 4:
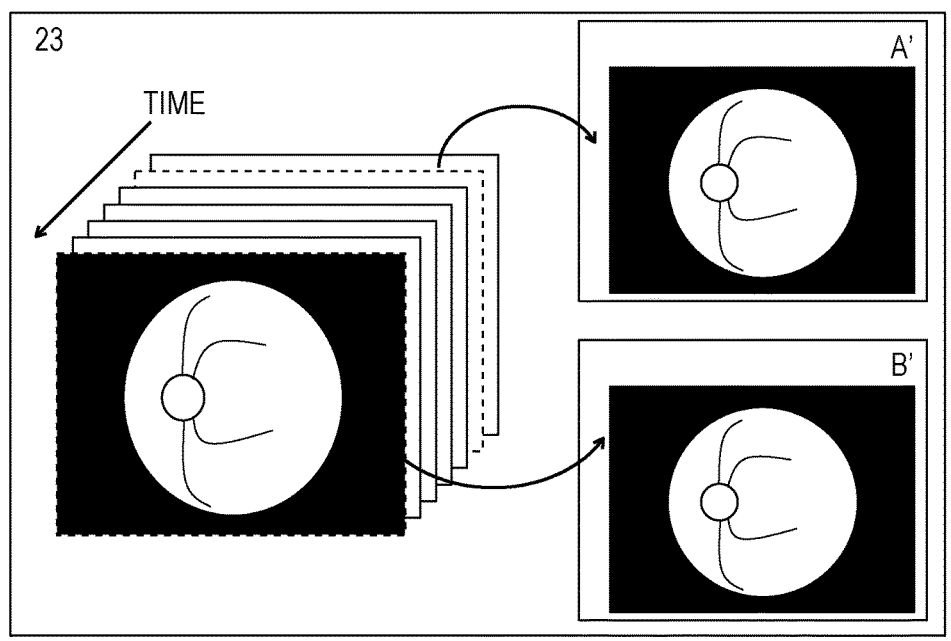
FIG. 4 is a diagram associated with a time when images are selected in the present embodiment.

FIG. 3 illustrates a method for selecting images for which subtraction is to be performed. Images stored in memory means are arranged horizontally on an imaging date basis and a first image A and a second image B may be selected from among the images using a mouse, a touch panel, or the like. There may also be a third image C and a fourth image D as images to be selected here. This has an effect in that the number of pieces of data may be increased in the case where there are a plurality of images to be compared with or when a change over time is checked. In addition, in the method for selecting, a plurality of images may be temporally arranged in a depth direction, and the first image A, which has been selected from among the plurality of images, may be displayed in such a manner that, for example, the first image A is zoomed and displayed on the right side as in FIG. 4. FIG. 4 illustrates images arranged in an anterior-posterior direction on the imaging date basis, and a selection may be made from among the images. This has an advantage in that an image may be displayed in a zoomed manner even in the case where there are many captured images and in that images whose imaging dates differ may be easily selected.

Subtraction Generation Flow

Figure 5:
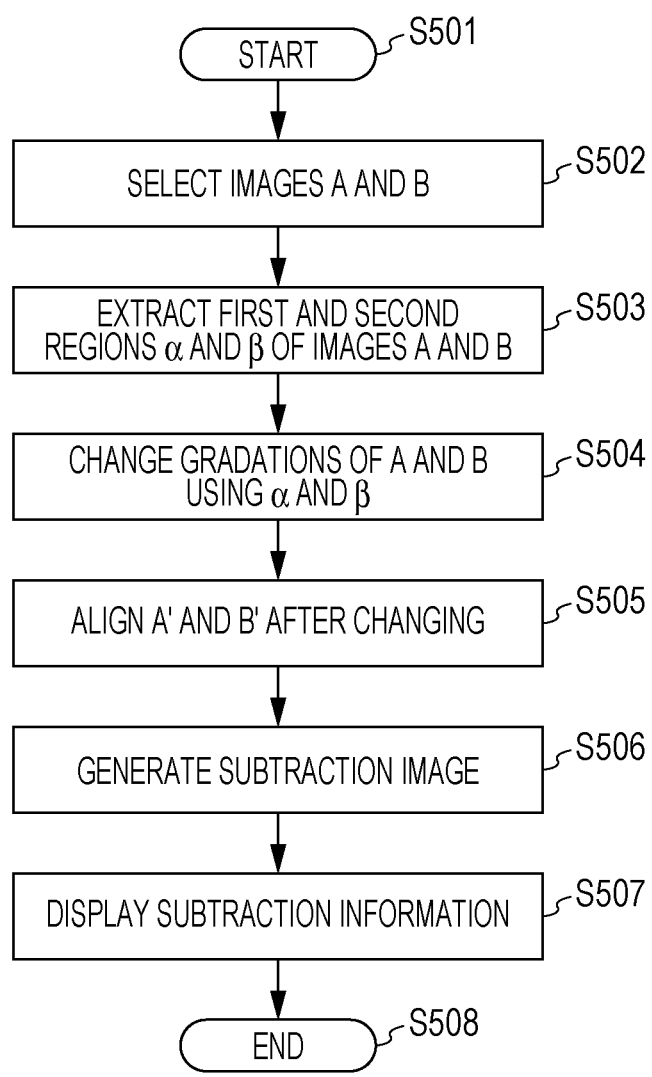
FIG. 5 is a flowchart for subtraction generation of the present embodiment.
Figure 6:
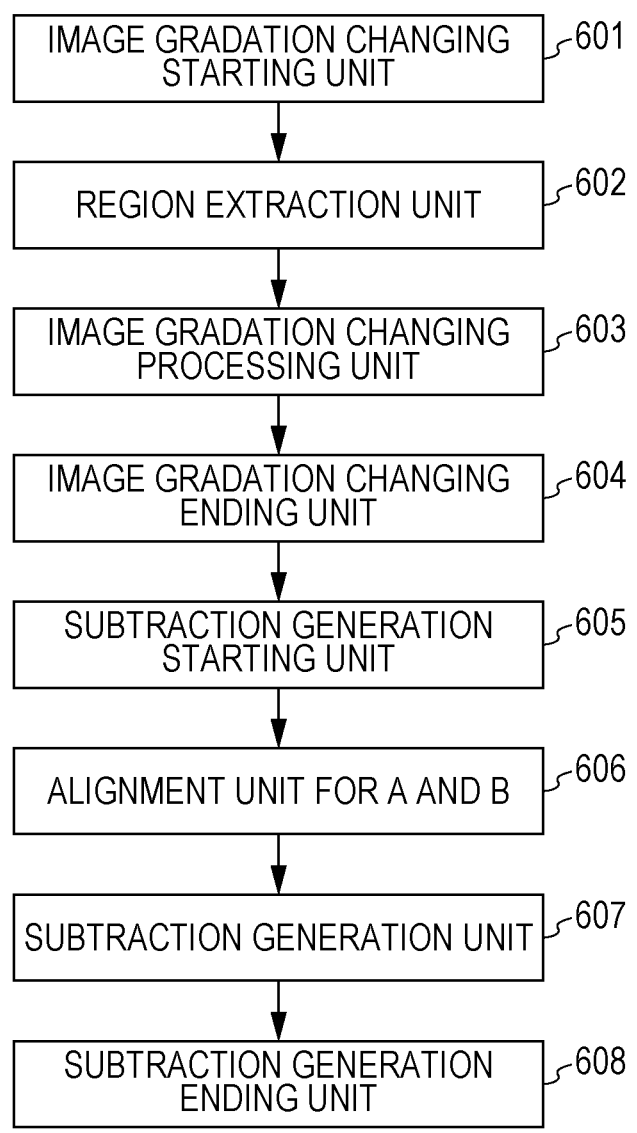
FIG. 6 is a block diagram for subtraction generation of the present embodiment.

FIGS. 5 and 6 are a flowchart and a block diagram for generating a subtraction image using captured images, respectively. A subtraction generation flow in the present embodiment includes an image gradation changing section and a subtraction generation section. First, the image gradation changing starting unit 601 starts a subtraction generation flow for the first image A and the second image B (S501), the first image A and the second image B being stored in the image memory 24, the first image A and the second image B being images of the same eye, the second image B being captured on a date different from that of the first image A. Next, the region extraction unit 602, which is an example of determination means, extracts, using extraction means, a first region α of the first image A and extracts a second region β of the second image B in an interlocked manner, the second region corresponding to the first region α (S502). Here, desirably, the first region α is an image region corresponding to a blood vessel of the fundus image Er'. This is because, in an autofluorescence image, a blood vessel in a blood vessel portion generally absorbs light of wavelengths that has passed through the autofluorescence exciter filter 10 and the blood vessel portion does not show autofluorescence. In addition, a standard position is determined using fundus pattern specifying means in the fundus image Er', the standard position is set to be an origin, an x axis and a y axis are set by considering rotation and movement of an image, and corresponding regions are regions that have the same x coordinate and the same y coordinate from the origin. Here, the standard position is, for example, an optic disk portion or a blood vessel portion of a fundus image. For example, in the case where a blood vessel portion is set to be a standard position, Japanese Patent Laid-Open No. 5-253215 may be cited as an example.

Figure 7A:
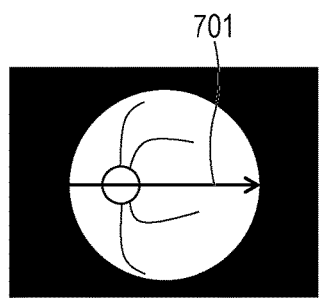
FIGS. 7A to 7E are diagrams illustrating pixel brightness value versus image height of the present embodiment.
Figure 7B:
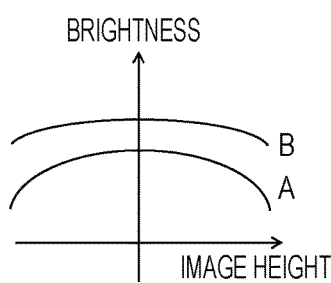
Figure 7C:
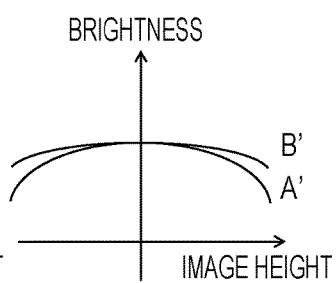
Figure 7D:
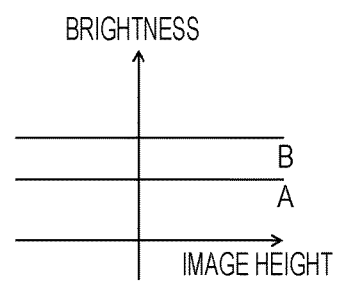
Figure 7E:
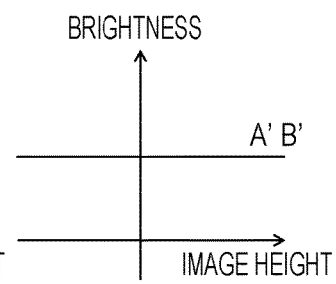

Note that, when imaging is performed in a state in which the pupil Ep of the eye E to be inspected is sufficiently open and sufficient alignment has been achieved, a region different from the first region α may be extracted as the second region β if the fundus image of FIG. 7A is, for example, unlike in FIG. 7B, an image whose brightness information with respect to image height at 701 is constant as in FIG. 7D, and in which shading (a state in which a portion surrounding a central portion is darker than the central portion) does not occur. This is because, in the case where shading exists as in FIG. 7B, there is a difference in brightness with respect to image height in the first region α, which is to be extracted. Here, supposing that central portions are made to match in terms of brightness by gradation changing, the central portions are well made to match in terms of brightness with respect to image height (FIG. 7C); however, a diagnosis-possible region is a limited region in the central portions. Thus, in the case of, for example, FIG. 7B, since a diagnosis area is limited, the first region α and the second region β need to be regions that correspond to each other. However, when the brightness with respect to image height is constant as in FIG. 7D, since the brightness of the first region α is constant at any image height, the second region β does not have to be at a position that corresponds to the first region α. In addition, in the case of, for example, FIG. 7E acquired by performing gradation changing for FIG. 7D, the image regions are entirely well matched also in the surrounding portion in terms of brightness, and thus the entirety of each of the image regions is a diagnosis-possible region.

Figure 9:
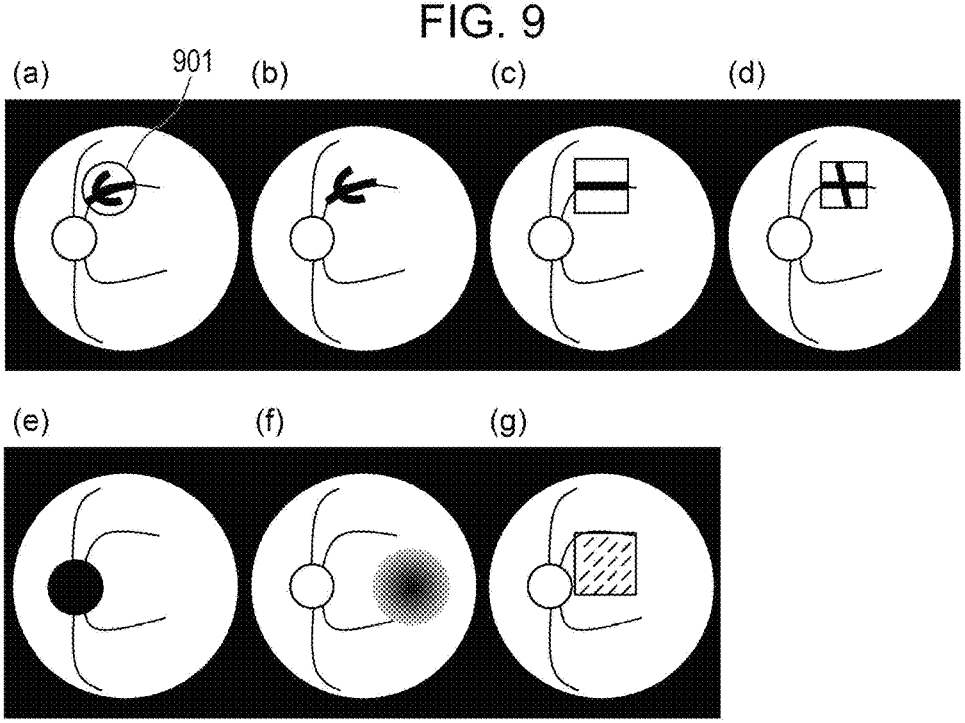
FIG. 9 includes diagrams associated with an extraction unit of the present embodiment.

Here, although the first region α is desirably a blood vessel portion, the first region α may also be extraction examples (a) to (g) illustrated in FIG. 9. (a) illustrates an example in which an examiner specifies an image region 901 including a blood vessel portion corresponding to a blood vessel of the fundus image Er', which has been captured, and the region extraction unit 602, which extracts the first region α, extracts the blood vessel portion corresponding to the blood vessel of the fundus image Er', which has been captured, from the specified image region 901. As a result, an effect may be expected in that the degree of freedom of analysis is increased by allowing a user to freely select the first region α. (b) illustrates an example in which the region extraction unit 602 automatically extracts the blood vessel portion corresponding to the blood vessel of the fundus image Er', which has been captured. As a result, a user does not have to select the first region α, an analysis time may be shortened, and a diagnosis support effect may be expected when the user is an unskilled person.

In addition, the form of a blood vessel to be selected may be, for example, as in (c) or (d). (c) illustrates an example in which a blood vessel to be extracted does not have a crossing portion and is a single blood vessel portion. This illustrates an example in which the first region α to be selected may be extracted if a region corresponds to a blood vessel. (d) illustrates an example in which blood vessels to be extracted cross with each other. This may be easily detected in the case of automatic extraction, and an effect may be expected in that a user easily selects an identical portion even in the case of manual selection and extraction. In addition, as in (e) to (g), an optic disk portion (e) corresponding to the optic disk of the fundus image Er', which has been captured, a macula portion (f) corresponding to a macula, and a normal nerve fiber layer portion (g) corresponding to a normal nerve fiber layer may also be extracted. In many cases, (e) and (f) are circular and are characteristic portions in a fundus image. Thus, an effect may be expected in that a user easily makes a selection, and, for (g), an effect may be expected in that a region to be extracted may be freely selected.

Figure 10A:
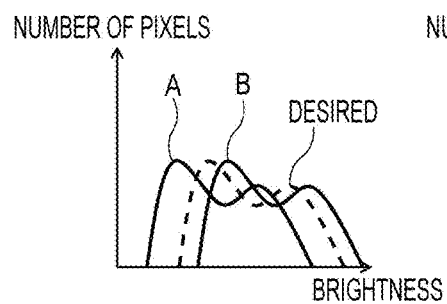
FIGS. 10A to 10D are diagrams illustrating image brightness before and after gradation changing of the present embodiment.
Figure 10C:
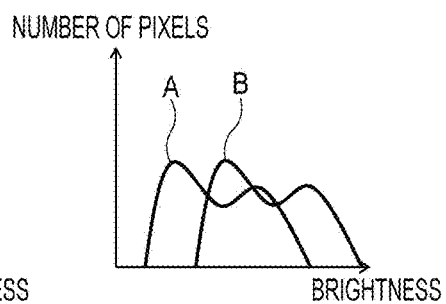
Figure 10B:
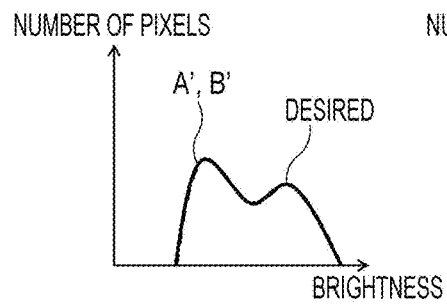
Figure 10D:
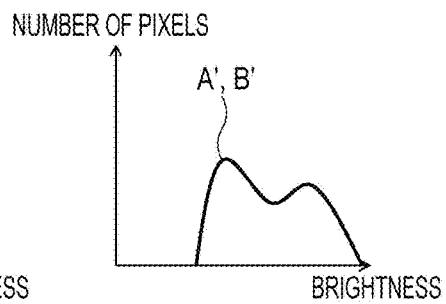

Next, the image gradation changing unit 603, which is an example of the changing means, calculates, using coefficient calculation means, a coefficient with which the first region α and the second region β are to have a desired brightness, and performs gradation changing on at least one of the gradation of the first image A and the gradation of the second image B using the coefficient (S503). FIGS. 10A to 10D illustrate examples of a histogram in the case where gradation changing has been performed. For a histogram of FIG. 10A, an example is illustrated in which the image gradation changing unit 603 performs gradation changing on the first image A and the second image B such that the first region α and the second region β have a desired brightness, and a histogram of FIG. 10B is acquired. For a histogram of FIG. 10C, an example is illustrated in which the image gradation changing unit 603 performs gradation changing on the first image A such that the first region α has the same brightness as the second region β, and a histogram of FIG. 10D is acquired.

The image gradation changing ending unit 604 ends image changing processing, and subsequently the subtraction generation starting unit 605 starts subtraction generation.

In addition, for images acquired after gradation changing, the alignment unit 606 aligns a first image A', which is acquired after gradation changing, and a second image B', which is acquired after gradation changing (S505). Here, alignment processing is performed using the above-described fundus pattern specifying means. A standard position is determined using the fundus pattern specifying means, the standard position is set to be an origin, an x axis and a y axis are set by considering rotation and movement of an image. Alignment is performed such that x axes are made to match and y axes are made to match. As a result, a subtraction image may be generated using the entirety of each of the image regions, and furthermore, a subtraction image may be generated using a plurality of images, which are more than or equal to two images, in a similar process.

In addition, the subtraction generation unit 607, which is an example of the generation means, generates a subtraction image (S506). A difference may be quantitatively visualized by generating a subtraction image, and a diagnosis effect may be improved. Next, a subtraction information display causes the display 23 to display subtraction information on the image A' and the image B' (S507), the image A' being acquired by performing gradation changing on the first image A, the image B' being acquired by performing gradation changing on the second image B, examples of the display 23 including a display and a monitor. In the end, the subtraction generation ending unit 608 ends the subtraction generation flow (S508).

Figure 8A:
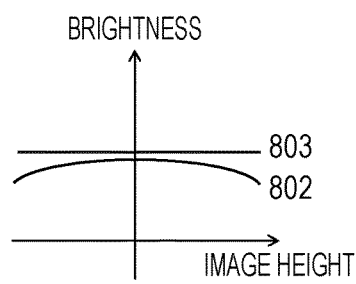
FIGS. 8A and 8B are diagrams associated with shading correction of a pupil diameter of the present embodiment.
Figure 8B:
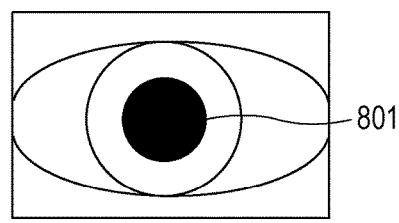

Note that in addition to the above-described gradation changing, shading correction may also be performed on the first image A and the second image B. FIGS. 8A and 8B illustrate diagrams for shading correction using the pupil diameter of the eye E to be inspected. Generally, it is known that in the case where an image of the fundus Er of the eye E to be inspected is captured, when the pupil diameter of the eye E to be inspected is small, shading occurs in a peripheral portion of the image due to vignetting of luminous flux. Image brightness with respect to image height of an image in which shading has occurred is denoted by 802 in contrast to 803 in FIG. 8A, and brightness decreases at a portion having a higher image height than the central portion. Thus, for example, when an anterior ocular segment is observed, a correction unit, which is not illustrated, may extract the pupil diameter (801) from an anterior ocular segment image of the eye E to be inspected and calculate shading expected on the basis of the extracted pupil diameter, and may also perform correction.

Display Method

Figure 11A:
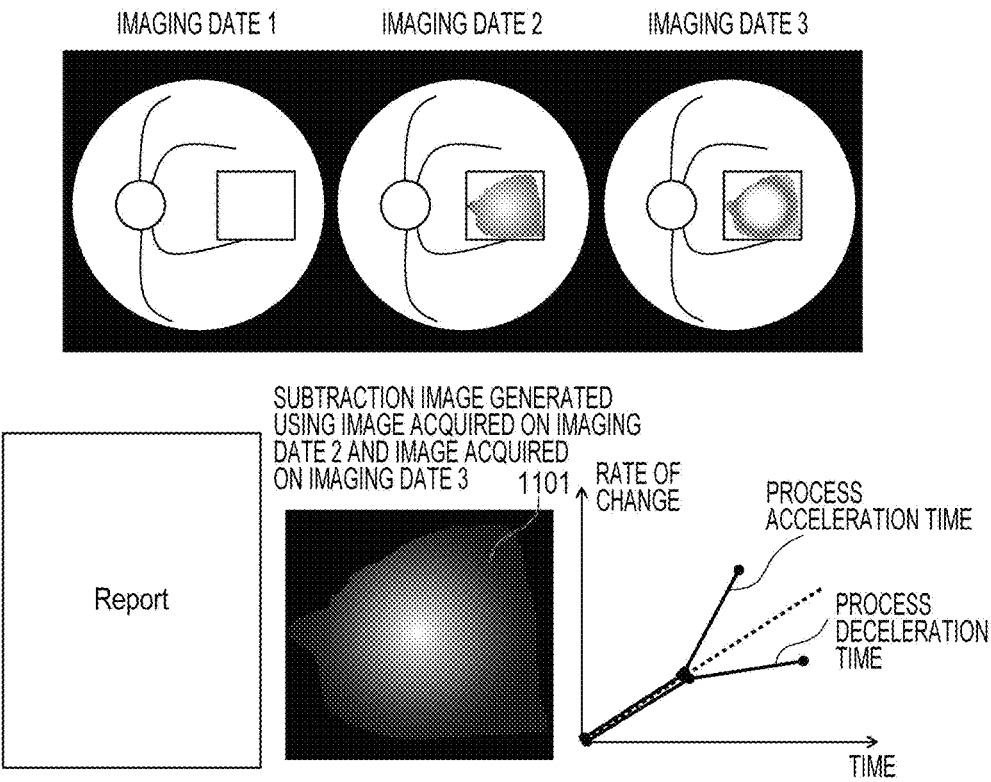
FIGS. 11A and 11B are diagrams associated with display of subtraction information of the present embodiment.
Figure 11B:
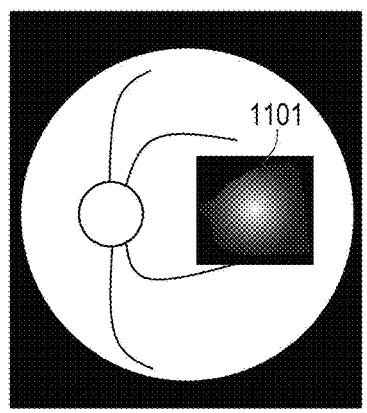

Here, a display example (S507) is illustrated in FIGS. 11A and 11B. In the display example, report information is displayed in which the above-described analysis results are collected. Specifically, information acquired at the time of image changing and subtraction information calculated using calculation means are displayed (1101), the information acquired at the time of image changing being such as a patient ID (Patient ID), gender, a disease name, a day of analysis (Date), the position and brightness value of each of the first region α and the second region β extracted by the extraction means, and a coefficient calculated by the coefficient calculation means. As a result, information for facilitating performance of similar image processing next time may be provided in addition to information usually used by a user to conduct a diagnosis.

In addition, an imaging date of an image, which has been captured, is displayed at a position above the image on the display 23. That is, a display controller causes a plurality of fundus images to be displayed in time series in a three-dimensional manner (arranged and displayed along a time axis) in accordance with imaging dates of the first and second fundus images acquired by performing autofluorescence imaging on the fundus at different times. In addition, as an example for illustrating a change in a disease portion in time series, a difference image acquired using a combination of two images that have been selected by a user from among selected images is displayed. In addition, a line graph is displayed illustrating changes in time series regarding a change in a rate of change of a specific brightness region calculated utilizing a subtraction image generated using two images whose dates are close to each other among the selected images.

Furthermore, a color map generation unit, which is not illustrated, generates and displays a pseudo color corresponding to a brightness value. As a result, difference information may be visually displayed. In addition, a user may also select an ROI. As a result, it is expected to provide an effect in that a change within the ROI is easily determined. In addition, even regarding information on the inside of the ROI, a line graph may be displayed illustrating changes in time series regarding a change in a rate of change of the specific brightness region. As a result, a time needed to conduct a diagnosis may be shortened since information on only a disease portion in which a user is interested may be displayed.

Ophthalmic Imaging Apparatus According to Another Present Embodiment

Note that an ophthalmic imaging apparatus according to the other present embodiment may correct a brightness difference between images by performing gradation changing to acquire a desired brightness using image information of the first region of the first image and the second region of the second image corresponding to the first region, the brightness difference between images having been generated because of imaging conditions. In addition, a subtraction image is generated using the first image and the second image, which have been acquired by performing gradation changing such that the brightness of the first region and that of the second region become equal to a desired brightness, and the amount of change in a hyperfluorescence region and that in a low fluorescence region are estimated. In addition, as a result of performing of color display in accordance with a brightness gradation, this ophthalmic imaging apparatus makes it possible to draw a change in a disease region using a pseudo color and determine a change in the form of the disease portion. In addition, the first region and the second region may be extracted either manually or automatically in the ophthalmic imaging apparatus according to the other present embodiment. In the case of manual extraction, there are advantages in that a user may specify a desired image region as the first region and the degree of freedom of analysis is increased. These are especially effective when the user is a skilled person or the like. In contrast, in the case of automatic extraction, labor may be reduced, and also automatic extraction is especially effective as a diagnosis support tool when the user is an unskilled person or the like. In addition, information on a disease portion in which a user is interested may be displayed by selecting an ROI (Region of Interest: a region of interest). Thus, a time needed to conduct a diagnosis may be shortened. In addition, the ophthalmic imaging apparatus according to the other present embodiment aligns a plurality of images of the same fundus such that the positions of characteristic points in the images match. In addition, a first region and an ROI of one image is specified, and a second region, which corresponds to the first region, and an ROI of another image may be specified on the basis of the first region and a result of image alignment. As a result, a complicated operation may be prevented in which the first region is specified in the plurality of images, and labor involved in the operation may be reduced. Furthermore, the ophthalmic imaging apparatus according to the other present embodiment may generate a subtraction image for each of a plurality of gradation changed images of the same eye, may specify ROIs that correspond to each other in individual subtraction images, and may calculate, for each ROI, the number of pixels of a hyperfluorescence region and the number of pixels of a low fluorescence region and display the numbers of pixels as time-series change information. Thus, it is possible to effectively support determination of changes in time series in the ROI, and the ophthalmic imaging apparatus according to the other present embodiment is especially effective as a diagnosis support tool.

Other Embodiments

In addition, the present invention is also realized by executing the following process. That is, the following process is a process in which a software program (program) that realizes functions of the above-described embodiments is supplied to a system or an apparatus via a network or various recording medium and the program is read and executed by a computer of the system or of the apparatus (or a CPU, an MPU, or the like).

According to the present invention, first, a subtraction image may be generated using a partial region of a first fundus image and a partial region of a second fundus image, the partial regions corresponding to each other, the first fundus image and the second fundus image having been acquired at different times by performing autofluorescence imaging on the fundus of an eye to be inspected. Then, display means may be caused to display an image generated by superimposing information regarding the subtraction image (the subtraction image itself or the like) at a position corresponding to the first and second regions on a fundus image acquired by performing autofluorescence imaging on the fundus of the eye to be inspected. As a result, it is easier for a user to determine which portion of a fundus image corresponds to the position of a region where a change in lipofuscin has occurred over time. Thus, in the case where a user checks changes in lipofuscin that have occurred over time using a subtraction image, checking of the position of a region may be facilitated where a change in lipofuscin has occurred over time in a fundus image.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of International Patent Application No. PCT/JP2013/067842, filed Jun. 28, 2013, which is hereby incorporated by reference herein in its entirety.

The invention claimed is:

1. An image processing apparatus comprising:
a region extraction unit configured to extract a blood vessel portion of a first fundus image acquired by performing autofluorescence imaging on a fundus of an eye to be inspected and the blood vessel portion of a second fundus image acquired by performing autofluorescence imaging on the fundus of the eye to be inspected at a time different from that of the first fundus image;
an image gradation processing unit configured to perform, using brightness of the blood vessel portion of the first fundus image and brightness of the blood vessel portion of the second fundus image, gradation changing on at least one of the first and second fundus images such that a brightness difference, between the blood vessel portion of the first fundus image and the blood vessel portion of the second fundus image, is reduced;
an alignment processing unit configured to align the first fundus image with the second fundus image by positioning the blood vessel portion of the first fundus image and the blood vessel portion of the second fundus image;
an image generation unit configured to generate a subtraction image subtracted between different regions of the first and second fundus images after the gradation processing and the alignment processing, the different regions being different from the blood vessel portion of the first fundus image and the blood vessel portion of the second fundus image; and
a display control unit configured to cause a display to display the first or second fundus image which superimposes the subtraction image on at least one of the different regions.

2. The image processing apparatus according to claim 1, further comprising:
an image superimposition unit configured to superimpose at least one of the subtraction image and a display form illustrating a position of the subtraction image on the fundus image.

3. The image processing apparatus according to claim 2, wherein the image superimposition unit superimposes the display form illustrating the position at the position on the fundus image, and
the display control unit causes the display to arrange and display a superimposition image generated by performing superimposition and the subtraction image.

4. The image processing apparatus according to claim 1, wherein the generation unit
generates a subtraction image using the first and second fundus images, and
a region having an intensity greater than or equal to a certain intensity in the subtraction image generated using the first and second fundus images is generated as the subtraction image.

5. The image processing apparatus according to claim 1, wherein the display control unit causes the display to display the first and second fundus images, and
a display form illustrating the second region to be displayed on the second fundus image.

6. The image processing apparatus according to claim 1, wherein the display control unit causes the first and second fundus images to be arranged and displayed along a time axis.

7. The image processing apparatus according to claim 1, wherein the display control unit causes the first and second fundus images to be displayed in time series in a three-dimensional manner in accordance with imaging dates of the first and second fundus images.

8. The image processing apparatus according to claim 1, further comprising:

a selection unit configured to select the first and second fundus images from among a plurality of fundus images acquired by performing autofluorescence imaging on the fundus; and an alignment unit configured to align the first and second fundus images using certain regions of the first and second fundus images, wherein the generation unit generates the subtraction image using the aligned first and second fundus images.

9. The image processing apparatus according to claim 1, further comprising:

a correction unit configured to correct shading of the first and second fundus images on the basis of a pupil diameter of an anterior ocular segment image of the eye to be inspected.

10. The image processing apparatus according to claim 1 in an ophthalmic system in which the image processing apparatus is connected to an ophthalmic imaging apparatus that performs autofluorescence imaging on the fundus of the eye to be inspected such that communication is possible, the image processing apparatus further comprising:

an acquisition unit configured to acquire fundus image data transmitted from the ophthalmic imaging apparatus.

11. An ophthalmic imaging apparatus comprising:

an illumination optical system configured to illuminate an eye to be inspected;

an imaging optical system configured to capture an image of a fundus of the eye to be inspected, on the basis of light returned from the eye to be inspected which is illuminated by the illumination optical system;

a selection unit configured to select an autofluorescence imaging mode in which autofluorescence imaging is performed on the fundus;

a wavelength selection unit configured to be inserted, in a case where the autofluorescence imaging mode has been selected, into at least one of the illumination optical system and the imaging optical system;

a region extraction unit configured to extract a blood vessel portion of a first fundus image acquired by performing autofluorescence imaging on the fundus using the imaging optical system and the blood vessel portion of a second fundus image acquired by performing autofluorescence imaging on the fundus using the imaging optical system at a time different from that of the first fundus image;

an image gradation processing unit configured to perform, using brightness of the blood vessel portion of the first fundus image and brightness of the blood vessel portion of the second fundus image, gradation changing on at least one of the first and second fundus images such that a brightness difference, between the blood vessel portion of the first fundus image and the blood vessel portion of the second fundus image, is reduced;

an alignment processing unit configured to align the first fundus image with the second fundus image by positioning the blood vessel portion of the first fundus image and the blood vessel portion of the second fundus image;

a generation unit configured to generate a subtraction image between different regions of the first and second fundus images after the gradation processing and the alignment processing, the different regions being different from the blood vessel portion of the first fundus image and the blood vessel portion of the second fundus image; and a display control unit configured to cause a display means to display the first or second fundus image which superimposes the subtraction image on at least one of the different regions.

12. The ophthalmic imaging apparatus according to claim 11, wherein the wavelength selection unit includes an autofluorescence exciter filter, which is insertable into and removable from an optical path of the illumination optical system, and an autofluorescence barrier filter, which is insertable into and removable from an optical path of the imaging optical system.

13. An image processing method comprising:

a step of a blood vessel portion of a first fundus image acquired by performing autofluorescence imaging on a fundus of an eye to be inspected and the blood vessel portion of a second fundus image acquired by performing autofluorescence imaging on the fundus of the eye to be inspected at a time different from that of the first fundus image;

a step of performing, using brightness of the blood vessel portion of the first fundus image and brightness of the blood vessel portion of the second fundus image, gradation changing on at least one of the first and second fundus images such that a brightness difference, between the blood vessel portion of the first fundus image and the blood vessel portion of the second fundus image, is reduced;

a step of aligning the first fundus image with the second fundus image by positioning the blood vessel portion of the first fundus image and the blood vessel portion of the second fundus image, a step of generating a subtraction image subtracted between different regions of the first and second fundus images after the graduation processing and the alignment processing, the different regions being different from the blood vessel portion of the first fundus image and the blood vessel portion of the second fundus image; and a step of controlling a display to display the first or second fundus image that superimposes the subtraction image on at least one of the different regions.

14. The image processing method according to claim 13, further comprising:

a step of superimposing at least one of the subtraction image and a display form illustrating a position of the subtraction image on the fundus image.

15. The image processing method according to claim 14, wherein in the step of superimposing, the display form illustrating the position is superimposed at the position on the fundus image, and in the step of causing, the display is caused to arrange and display a superimposition image generated by performing superimposition and the subtraction image.

* * * * *